US011628336B2

(12) United States Patent
Tsukada et al.

(10) Patent No.: US 11,628,336 B2
(45) Date of Patent: Apr. 18, 2023

(54) EXERCISE EVALUATION IMPROVEMENT SYSTEM, AND EXERCISE EVALUATION IMPROVEMENT METHOD

(71) Applicant: NIPPON TELEGRAPH AND TELEPHONE CORPORATION, Tokyo (JP)

(72) Inventors: Shingo Tsukada, Tokyo (JP); Hiroshi Nakashima, Tokyo (JP); Tetsuomi Sogawa, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 72 days.

(21) Appl. No.: 16/969,150

(22) PCT Filed: Feb. 13, 2019

(86) PCT No.: PCT/JP2019/005041
§ 371 (c)(1),
(2) Date: Aug. 11, 2020

(87) PCT Pub. No.: WO2019/159951
PCT Pub. Date: Aug. 22, 2019

(65) Prior Publication Data
US 2021/0038945 A1 Feb. 11, 2021

(30) Foreign Application Priority Data
Feb. 13, 2018 (JP) .............................. JP2018-023577

(51) Int. Cl.
*A63B 24/00* (2006.01)
*G06N 20/00* (2019.01)
(Continued)

(52) U.S. Cl.
CPC .......... *A63B 24/0075* (2013.01); *A63B 69/36* (2013.01); *A63B 71/0622* (2013.01);
(Continued)

(58) Field of Classification Search
CPC . A63B 24/0075; A63B 69/36; A63B 71/0622; G06N 20/00
See application file for complete search history.

(56) References Cited

U.S. PATENT DOCUMENTS

| 5,111,410 A | 5/1992 | Nakayama et al. |
| 2014/0199672 A1* | 7/2014 | Davidson ........... A63B 21/0058 434/247 |
| 2018/0311530 A1* | 11/2018 | Kruger ............... A63B 24/0006 |

FOREIGN PATENT DOCUMENTS

| JP | H0326281 A | 2/1991 |
| JP | 8-224330 | 9/1996 |
| JP | 2017-55913 | 3/2017 |

OTHER PUBLICATIONS

Kuribayashi, Yasuo, "I only need impact sone for practice," Golf Digest Co., Ltd., 105-8670 Shinbashi 6, Minato-ku, Tokyo-18-5, 2016.
(Continued)

*Primary Examiner* — Robert P Bullington

(57) ABSTRACT

An exercise rating and improvement system comprising: a feature amount extraction unit for extracting, from information obtained from a subject, a feature amount about exercise efficiency; an rating unit for rating exercise efficiency of the subject by comparing the extracted feature amount and a feature amount to be compared; and an improvement information providing unit for providing, on the basis of the rating result, information such that the feature amount of the subject approaches the feature amount to be compared.

20 Claims, 13 Drawing Sheets

(51) Int. Cl.
*A63B 69/36* (2006.01)
*A63B 71/06* (2006.01)

(52) U.S. Cl.
CPC ...... *G06N 20/00* (2019.01); *A63B 2024/0012* (2013.01); *A63B 2024/0068* (2013.01); *A63B 2071/0625* (2013.01); *A63B 2071/0655* (2013.01); *A63B 2071/0694* (2013.01); *A63B 2220/56* (2013.01); *A63B 2220/803* (2013.01); *A63B 2220/808* (2013.01); *A63B 2220/836* (2013.01); *A63B 2225/74* (2020.08)

(56) References Cited

OTHER PUBLICATIONS

Kawashima, Kazuaki, "Studies on Movement Analysis of Golf Swing and Physical Characteristics of Golf Player," Doctoral Thesis (human science) Graduate School of Human Science, Waseda University, Jan. 2004.

* cited by examiner

EXERCISE EVALUATION IMPROVEMENT SYSTEM, AND EXERCISE EVALUATION IMPROVEMENT METHOD

CROSS-REFERENCE TO RELATED APPLICATIONS

This application is a U.S. 371 Application of International Patent Application No. PCT/JP2019/005041, filed on 13 Feb. 2019, which application claims priority to and the benefit of JP Application No. 2018-023577, filed on 13 Feb. 2018, the disclosures of which are hereby incorporated herein by reference in their entireties.

TECHNICAL FIELD

The present invention relates to an exercise rating and improvement system and an exercise rating and improvement method.

BACKGROUND ART

In various sports such as, for example, golf, tennis, and baseball, players learn the most reasonable postures or forms by training to achieve a certain improvement. Particular, in golf, in which the accuracy of the ball flying direction directly affects the score as the nature of sports, it is required to learn an accurate swing form.

Conventionally, to improve sports, such as golf, with repetitive motion, it is important to improve the exercise efficiency of the player. For improved sports, various instruction manuals have been published (see, for example, NPL 1). Whether the player is moving according to the instruction manual, however, largely depends on the subjectivity of the player. Therefore, there has been a problem that it is difficult to rate the exercise efficiency quantitatively and keep track of the improvement of the exercise efficiency objectively. There are also known techniques, such as attaching a marker to the player's body to take a video thereof and rating the exercise efficiency of the player from the marker's trajectories (motion capture) or providing various sensors to the player's body and analyzing the motion from the acquired data (see, for example, NPL 2).

CITATION LIST

Non Patent Literature

[NPL 1] Yasuo Kuribayashi, *Renshu wa Inpakuto zohn Dakecie Ii!* (All you need is practice in the impact zone!) Golf Digest Sha Co., Ltd., 24 Feb. 2016.
[NPL 2] Kazuaki Kawashima, *Gorufu Suingu no Dousa Bunseki to Gorufu Pureiyah no Shintai Tokusei ni Kansuru Kenkyu* (Studies on Motion Analysis of Golf Swing and Physical Characteristics of Golf Player), Graduate School of WASEDA University, Doctoral dissertation (Graduate School of Human Sciences), January 2004.

SUMMARY OF THE INVENTION

Technical Problem

Unfortunately, in the former technique, it is impossible to capture the trajectories of the marker if the player's motion prevents the marker from appearing in the video. In addition, in the latter technique, it is difficult to keep track of the improvement of the exercise efficiency on the basis of the results of the motion analysis, as with the instruction manual.

In view of the foregoing, the purpose of the present invention is to provide a technology for improving exercise efficiency.

Means for Solving the Problem

An aspect of the present invention is an exercise rating and improvement system comprising: a feature amount extraction unit for extracting, from information obtained from a subject, a feature amount about exercise efficiency; an rating unit for rating exercise efficiency of the subject by comparing the extracted feature amount and a feature amount to be compared; and an improvement information providing unit for providing, on the basis of the rating result, information such that the feature amount of the subject approaches the feature amount to be compared.

An aspect of the present invention is the above exercise rating and improvement system, wherein the feature amount extraction unit extracts, from information obtained via a machine learning from the subject, the feature amount about exercise efficiency.

An aspect of the present invention is the above exercise rating and improvement system, comprising one of a first sensor for acquiring biological information of the subject, a second sensor for acquiring information about a joint motion of the subject, a third sensor for acquiring information of a pressure applied on a plantar part of the subject, and a fourth sensor attached to a reference site during exercise of the subject and a site the distance of which is to be measured from the reference site, the fourth sensor being for acquiring information about a distance between the sites, wherein the feature amount extraction unit extracts, from information of the subject obtained from any of the above sensors, a feature amount about exercise efficiency.

An aspect of the present invention is an exercise rating and improvement method comprising: a feature amount extraction step of extracting, from information obtained from a subject, a feature amount about exercise efficiency, an rating step of rating exercise efficiency of the subject by comparing the extracted feature amount and a feature amount to be compared, and an improvement information providing step of providing, on the basis of the rating result, information such that the feature amount of the subject approaches the feature amount to be compared.

Effects of the Invention

The present invention may improve exercise efficiency.

DESCRIPTION OF EMBODIMENTS

Figure 1:
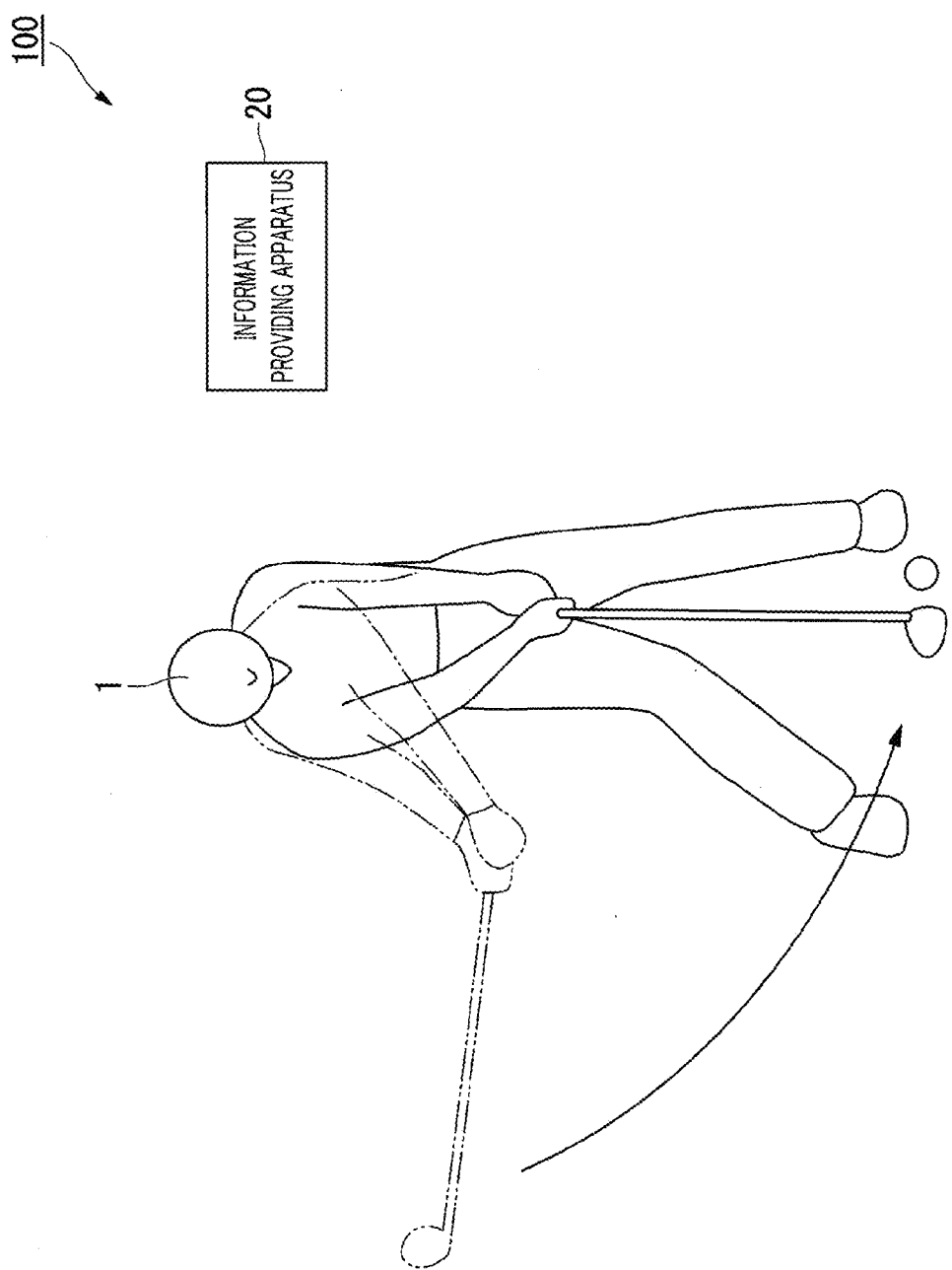
FIG. 1 is a configuration diagram representing the system configuration of an exercise rating and improvement system according to the present invention.

Embodiments of the present invention will be described below with reference to the drawings. FIG. 1 is a configuration diagram representing the system configuration of an exercise rating and improvement system 100 according to the present invention. The exercise rating and improvement system 100 includes a sensor (not shown in FIG. 1), a relay system (not shown in FIG. 1), and an information providing system 20. The sensor and the relay system 20 are connected in a wired or wireless manner. In addition, the relay system and the information providing system 20 communicate through a wired or wireless communication. Note that although the following description is given with respect to golf as sports to which the exercise rating and improvement system 100 may be applied, the exercise rating and improvement system 100 is also applicable to general sports including tennis and baseball, in addition to golf.

The sensor is attached to the subject 1 and measures biological information of the subject 1 and information about a motion of the subject 1. Here, the subject 1 is a person who is to be measured for the exercise rating. The sensor outputs the measurement results to the relay system. The relay system sends the measurement results measured by the sensor to the information providing system 20.

The information providing system 20 rates the exercise efficiency of the subject 1 on the basis of the measurement results and provides the rating result to the subject 1. In addition, the information providing system 20 provides the subject 1 with information about the improvement of the exercise efficiency based on the rating result and information about the improvement situation. Rating indices of the exercise efficiency include motion, position, timing, strength, and tension. In addition, when the exercise efficiency is rated as low, the information about the improvement of the exercise efficiency is information of motions to be performed to improve the items rated as low. In addition, the information about the improvement situation is information that indicates how much the exercise efficiency has been improved by performing the motions in accordance with the information about the improvement of the exercise efficiency. Specific configuration examples of the exercise rating and improvement system 100 according to the present invention will be described below.

Figure 2:
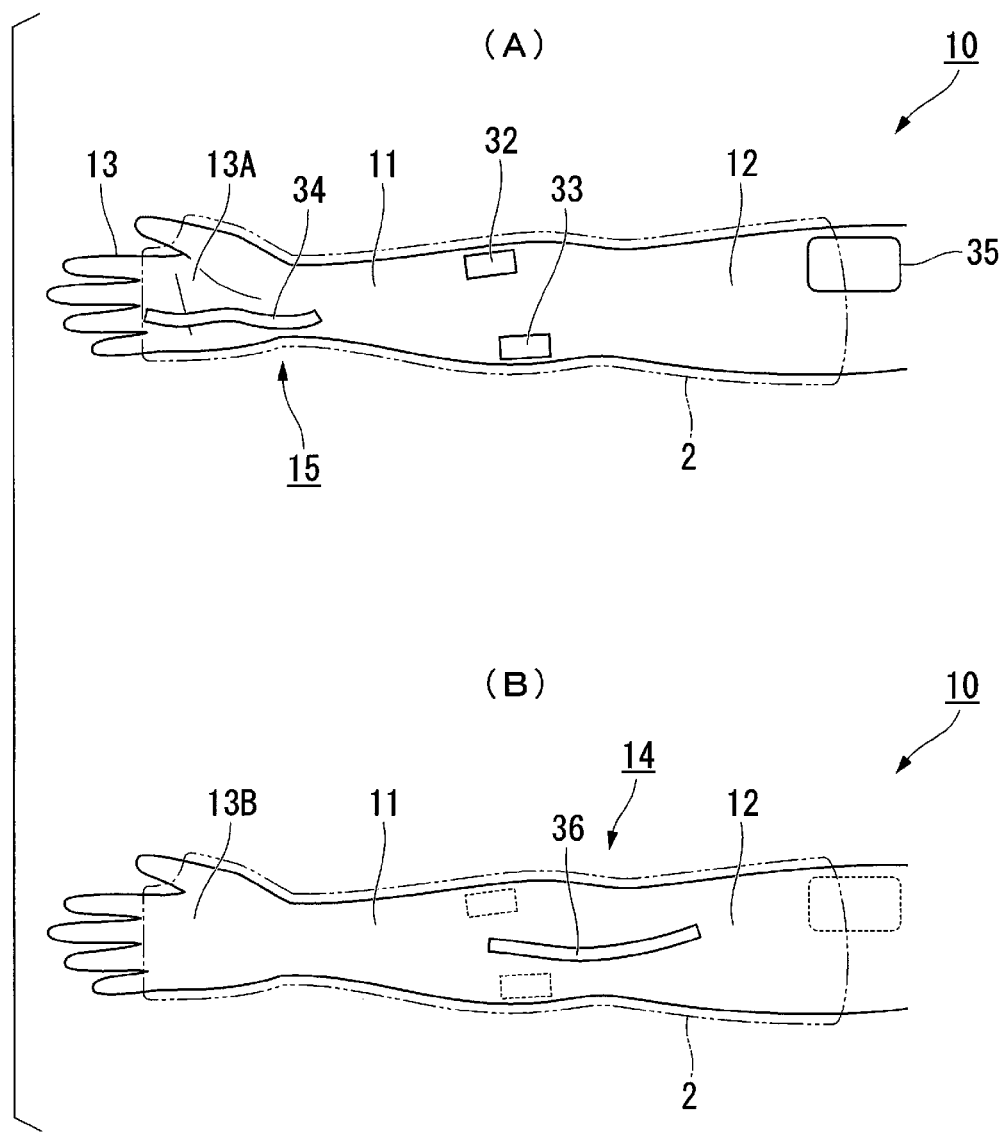
FIG. 2 illustrates examples of sensors in an exercise rating and improvement system according to a first embodiment.

(First Embodiment) FIG. 2 illustrates examples of sensors in an exercise rating and improvement system 100 according to a first embodiment. FIG. 2 (A) illustrates an example of sensors fixed to the palm side of an arm 10. FIG. 2 (B) illustrates an example of sensors fixed to the dorsum manus side of the arm 10. The exercise rating and improvement system 100 in the first embodiment includes, in addition to the information providing system 20, bioelectrodes 32 and 33 and stretch sensors 34 and 36, all of which are attached to the subject 1, and a relay system 35 that sends the measurement results of the sensors to the information providing system 20.

The sensors according to this embodiment are attached to the arm 10 of the subject 1. The sensors include a plurality of (two in this embodiment) bioelectrodes 32 and 33, a plurality of (two in this embodiment) stretch sensors 34 and 36, and a fixture (arm cover) 2 that contains the bioelectrodes 32 and 33 and stretch sensors 34 and 36. As shown in FIG. 2 (A), the bioelectrodes 32 and 33 and stretch sensor 34 are fixed on a front arm 11 by the fixture 2. In addition, the relay system 35 is fixed around an upper arm 12. In addition, as shown in FIG. 2 (B), the stretch sensor 36 is fixed around an elbow joint 14 by the fixture 2.

The bioelectrodes 32 and 33 acquire a biological signal of the subject 1. The biological signal is a signal of a potential variation from a living body such as an electrocardiogram, an electroencephalogram, and an electromyogram of the subject 1. The bioelectrodes 32 and 33 have a size of for example about 1 to 4 cm square. The bioelectrode 32 acquires the electromyogram of radial carpal muscles. In addition, the bioelectrode 33 acquires the electromyogram of ulnar carpal muscles.

The stretch sensor 34 is fixed on a palm 13A by the fixture 2. The stretch sensor 34 stretches and contracts with the motion of a wrist joint 15 and converts the amount of stretch and contraction to an electrical signal. Specifically, the stretch sensor 34 has elasticity and electrical conductivity. The stretch sensor 34 is made of an elastic body such as elastomer. The stretch sensor 34 according to this embodiment has a thin and elongated tape shape. The stretch sensor 34 has a variable capacitance in response to a change of the length and area caused by stretch and contraction. Specifically, the stretch sensor 34 converts its stretch to an electrical signal (capacitance change). Quantitative detection of the capacitance change may quantitatively measure the stretch amount (the amount of stretch and contraction). Note that the aspect of the stretch sensor 34 is not limited to the foregoing, and it is also possible to use a sensor that detects the stretch in different manners, such as a sensor having a variable resistance according to stretch and contraction.

The relay system 35 is electrically connected to the bioelectrodes 32 and 33, the stretch sensor 34, and the stretch sensor 36. The relay system 35 sends to the information providing system 20 an electrical signal (specifically, biological information and capacitance change) delivered from the bioelectrodes 32 and 33, the stretch sensor 34, and the stretch sensor 36. It is preferable to communicate between the relay system 35 and the information providing system 20 using, by way of example, a wireless communication that is compliant with the Bluetooth (registered trademark) specification. The stretch sensor 36 is fixed on the elbow joint 14 by the fixture 2. The stretch sensor 36 stretches and contracts with the motion of the elbow joint 14 and converts the amount of stretch and contraction to an electrical signal.

Figure 3:
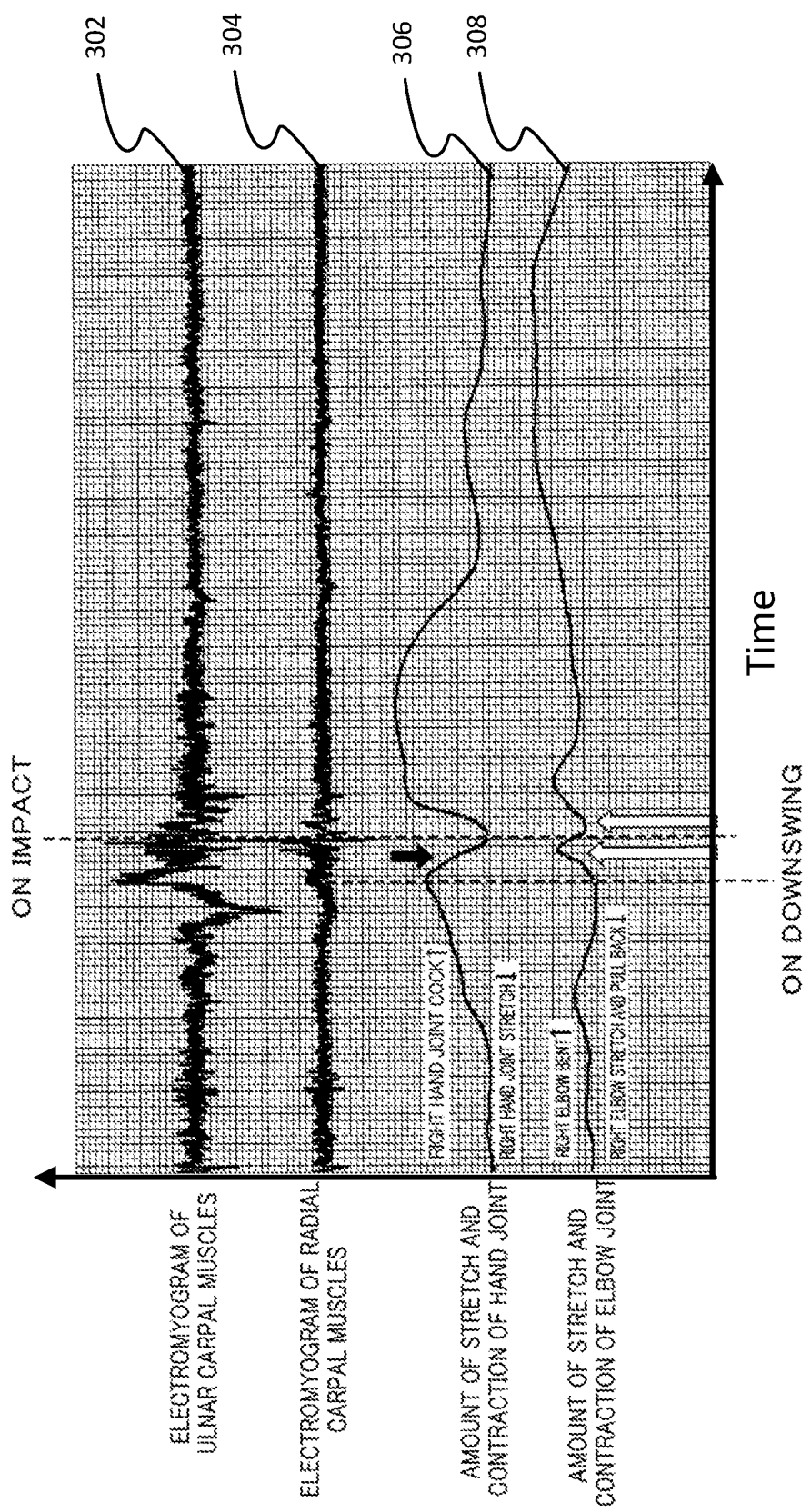
FIG. 3 illustrates measurement results of motions of a subject obtained by a plurality of sensors shown in FIG. 2.
Figure 4:
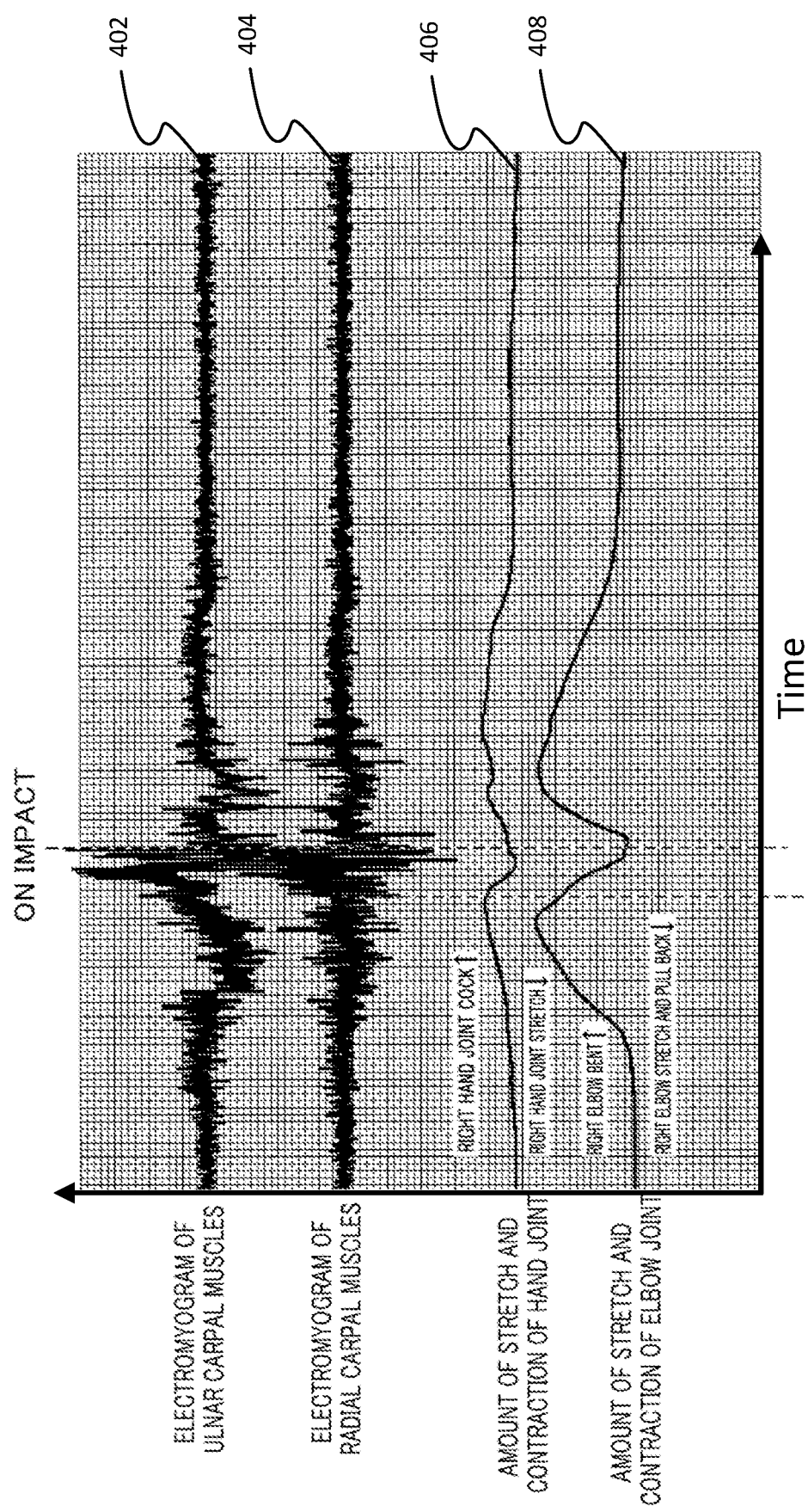
FIG. 4 illustrates measurement results of motions of a subject obtained by a plurality of sensors shown in FIG. 2.
Figure 5:
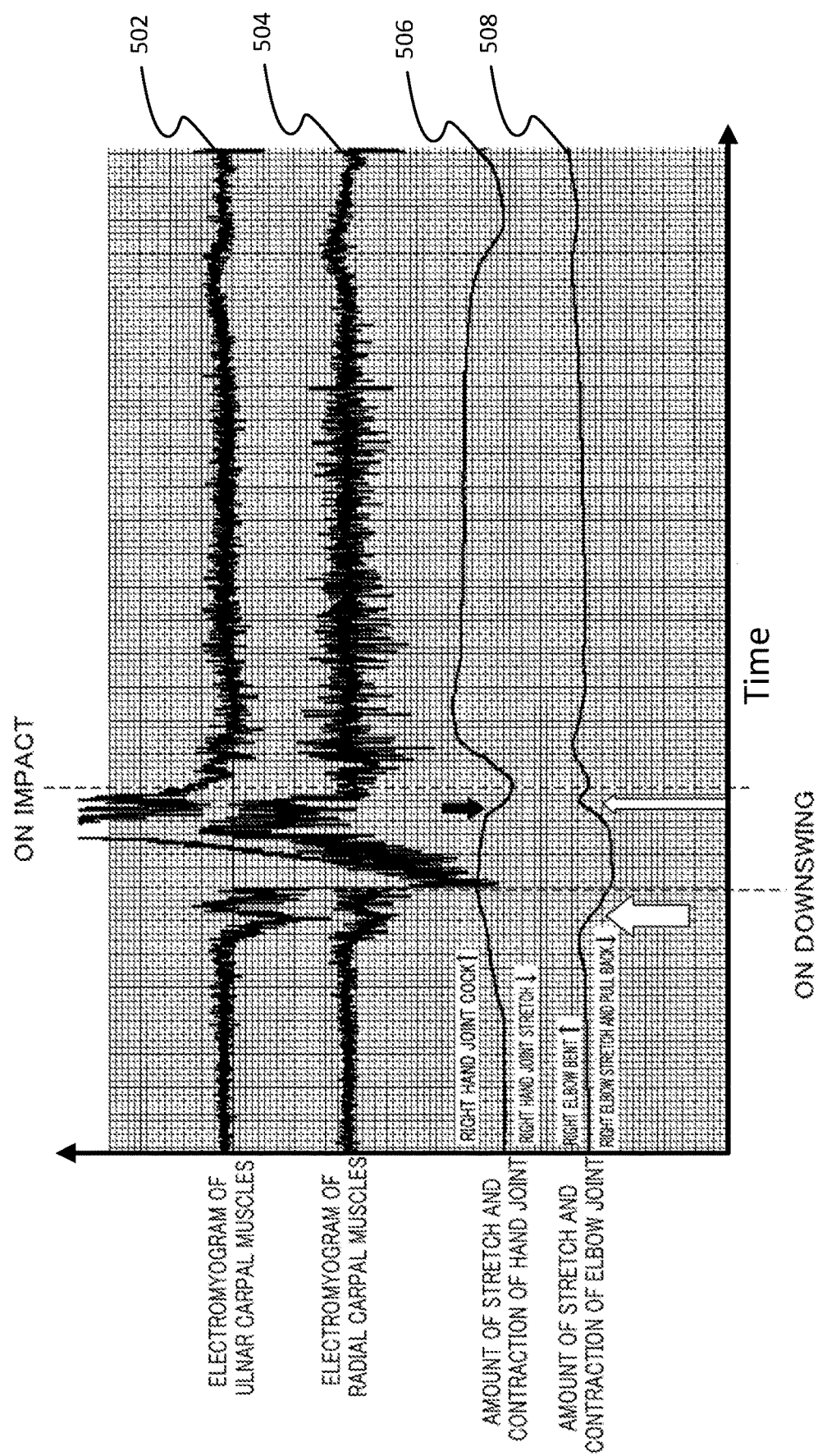
FIG. 5 illustrates measurement results of motions of a subject obtained by a plurality of sensors shown in FIG. 2.

FIGS. 3 to 5 illustrate measurement results of the motions of a plurality of subjects 1 obtained by the sensors shown in FIG. 2. FIG. 3 illustrates measurement results of the motions of a senior. FIG. 4 and FIG. 5 illustrate measurement results of the motions of a beginner and an intermediate.

Figure 6:
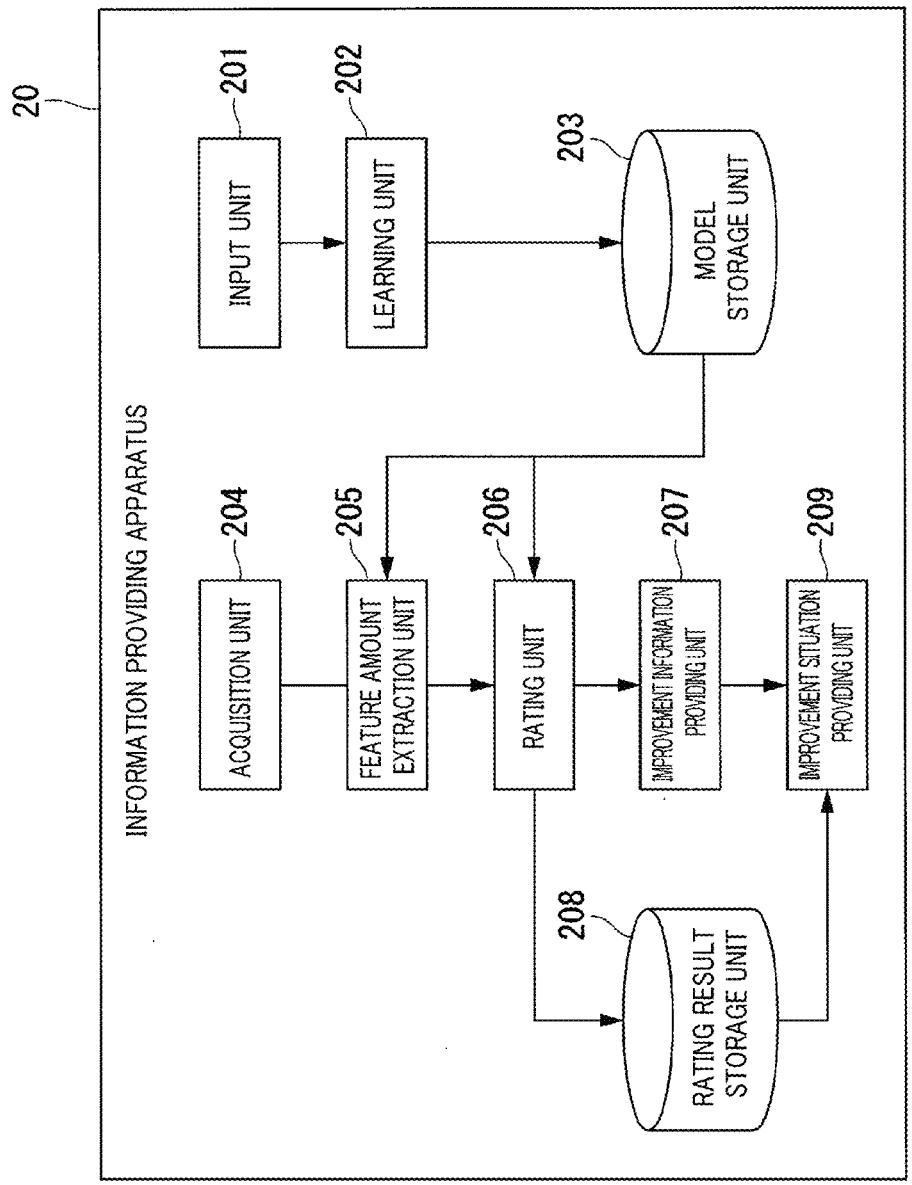
FIG. 6 is a schematic block diagram representing the function configuration of an information providing system.

FIG. 6 is a schematic block diagram representing the function configuration of the information providing system 20. The information providing system. 20 includes a central processing unit (CPU), a memory, and an auxiliary storage device or the like connected via a bus and runs an information providing program. Running the information providing program enables the information providing system. 20 to function as a system including an input unit 201, a learning unit 202, a model storage unit 203, an acquisition unit 204, a feature amount extraction unit 205, a rating unit 206, an improvement information providing unit 207, an rating result storage unit 208, and an improvement situation providing unit 209. Note that all or part of each function of the information providing system 20 may be achieved using hardware such as an application specific integrated circuit (ASIC), a programmable logic device (PLD), and a field programmable gate array (FPGA). In addition, the information providing program may be recorded in a computer-readable storage medium. The computer-readable storage medium includes a portable medium such as a flexible disk, a magneto-optical disk, a ROM, a CD-ROM, and a storage device such as a hard disk built in a computer system. In addition, the information providing program may be sent and receipt through an electrical communication line.

The input unit 201 inputs learning data. In this embodiment, supervised learning data is used as the learning data. The supervised learning data is, for example, a feature amount of measurement results of motions obtained from a senior in sports. Note that the supervised learning data is a feature amount obtained by attaching a sensor to a senior and measuring the motions of the senior via the sensor. The learning unit 202 generates a model by learning using learning data input from the input unit 201. The model storage unit 203 stores the model generated by the learning unit 202. The model storage unit 203 is configured using a storage device such as a magnetic hard disk drive or a semiconductor memory device.

The acquisition unit 204 acquires various information from the sensor. For example, the acquisition unit 204 acquires biological information and information of the amount of stretch and contraction. The acquisition unit 204 outputs the acquired information to the feature amount extraction unit 205. The feature amount extraction unit 205 uses the model stored in the model storage unit 203 to extract the feature amount from the information output from the acquisition unit 204. For example, the feature amount extraction unit 205 uses the model stored in the model storage unit 203 to extract the feature amount of biological information and information of the amount of stretch and contraction. As described above, the feature amount extraction unit 205 extracts the feature amount using the model obtained by the machine learning. The feature amount extraction unit 205 outputs the extracted feature amount to the rating unit 206.

The rating unit 206 rates the exercise efficiency of the subject 1 on the basis of the feature amount output from the feature amount extraction unit 205. Specifically, the rating unit 206 refers to the model stored in the model storage unit 203 and compares the acquired feature amount and the feature amount of the model. In so doing, the rating unit 206 uses, as the feature amount of the model, the feature amount of the same site as the site where the feature amount is acquired. The rating unit 206 rates the exercise efficiency as good if the correlation between the acquired feature amount and the feature amount of the model is greater than or equal to a predetermined threshold. Meanwhile, the rating unit 206 rates the exercise efficiency as bad if the correlation between the acquired feature amount and the feature amount of the model is less than a predetermined threshold. The rating unit 206 outputs the rating result, the acquired feature amount, and the feature amount of the model to the improvement information providing unit 207. The rating unit 206 also relates and stores the rating result, the acquired feature amount, and the feature amount of the model in the rating result storage unit 208.

The improvement information providing unit 207 provides the rating result and the improvement information to the subject 1. The improvement information providing unit 207 may provide the rating result in aspects including sound, vibration, light, and video. The improvement information providing unit 207 may also provide the improvement information in aspects including sound, vibration, light, video, numerical value, and table. The improvement information providing unit 207 provides to the subject 1, as the improvement information, information (for example, a method and a direction for improving the exercise efficiency) that eliminates the difference between the feature amount of the subject 1 and the feature amount of the model.

Here, with reference to FIGS. 3 to 5, a description is given of examples of the information provided by the improvement information providing unit 207. Specifically, examples are described where the information shown in FIGS. 3 to 5 is the feature amount obtained from the subject 1. In FIG. 3, the improvement information providing unit 207 provides information over time (i.e., Electromyogram of ulnar carpal muscles 302, electromyogram of radial carpal muscles 304, amount of strength and contraction of hand joint 306, and amount of stretch and contraction of elbow joint 308) in which an upward peak rises as the elbow joint bends on the downswing. A downward peak appears as the elbow joint stretches just before the impact. Information is provided including that the dorsiflexion (cock) of the right hand joint goes to palmar flexion in the reverse direction (wrist bent) on the downswing (before the impact).

In addition, in FIG. 4, the improvement information providing unit 207 provides information over time (i.e., Electromyogram of ulnar carpal muscles 402, electromyogram of radial carpal muscles 404, amount of strength and contraction of hand joint 406, and amount of stretch and contraction of elbow joint 408) including that the right hand joint cock is kept until just before the impact. In addition, in FIG. 5, the improvement information providing unit 207 provides information over time (i.e., Electromyogram of ulnar carpal muscles 502, electromyogram of radial carpal muscles 504, amount of strength and contraction of hand joint 506, and amount of stretch and contraction of elbow joint 808) including that the right elbow joint bends less and the right elbow stretches from the early downswing.

The rating result storage unit 208 relates and stores, for each subject 1, the rating result, the acquired feature amount, and the feature amount of the model. The rating result storage unit 208 is configured using a storage device such as a magnetic hard disk drive or a semiconductor memory device.

The improvement situation providing unit 209 compares the information stored in the rating result storage unit 208 and the improved information. The improvement situation providing unit 209 then provides to the subject 1, as the improvement situation, information indicating how the exercise efficiency is changed compared to the information stored in the rating result storage unit 208. Whether the information provided by the improvement information providing unit 207 is the improved information may be determined depending on whether the information of the subject 1 is already stored in the rating result storage unit 208. If, for example, the information of the subject 1 is already stored in the rating result storage unit 208, the improvement situation providing unit 209 determines that the information obtained from the improvement information providing unit 207 is the improved information. In addition, if the information of the subject 1 is not already stored in the rating result storage unit 208, the improvement situation providing unit 209 determines that the information obtained from the improvement information providing unit 207 is not the improved information. Note that if the information provided by the improvement information providing unit 207 is not the improved information, the improvement situation providing unit 209 does no processing.

The exercise rating and improvement system 100 thus configured according to the first embodiment compares the feature amount of the measurement results obtained during the exercise of the subject 1 and the feature amount of the measurement results obtained during the exercise of a senior, the feature amount being previously stored as a model. The exercise rating and improvement system 100 then rates the exercise efficiency of the subject 1 and provides information about the improvement of the exercise efficiency. The exercise efficiency may thus be improved.

Figure 7:
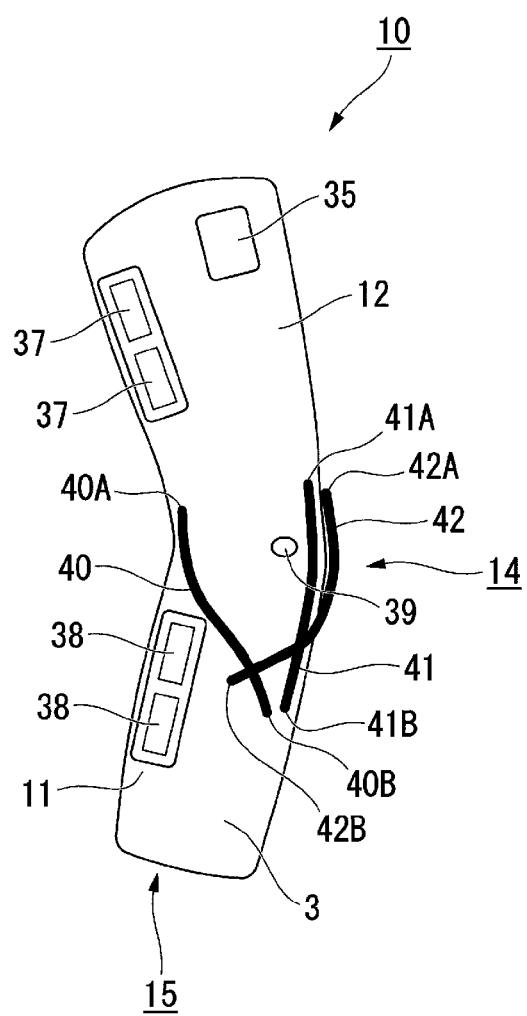
FIG. 7 illustrates an example of sensors in an exercise rating and improvement system according to a second embodiment.

(Second Embodiment) FIG. 7 illustrates an example of sensors in an exercise rating and improvement system 100 according to a second embodiment. The exercise rating and improvement system 100 in the second embodiment includes, in addition to the information providing system 20, a plurality of bioelectrodes 37 and 38, a marker 39, and a plurality of stretch sensors 40, 41, 42, all of which are attached to the subject 1, and the relay system 35, which sends the measurement results of the sensors to the information providing system 20.

The sensors according to this embodiment are attached to the arm 10 of the subject 1. The sensors include a plurality of (four in this embodiment) bioelectrodes 37 and 38, a marker 39, a plurality of (three in this embodiment) stretch sensors 40, 41, and 42, and a fixture (supporter) 3 that contains the bioelectrodes 37 and 38, the marker 39, and the stretch sensors 40, 41, and 42.

As shown in FIG. 7, the bioelectrodes 37 are fixed on the upper arm 12 by the fixture 3 and the bioelectrodes 38 are fixed on the front arm 11 by the fixture 3. In addition, the relay system 35 is fixed around the upper arm 12. In addition, as shown in FIG. 7, the marker 39 and the stretch sensors 40, 41, and 42 are fixed around the elbow joint 14 by the fixture 3.

The bioelectrodes 37 and 38 acquire a biological signal of the subject 1. The bioelectrodes 37 and 38 have a size of for example about 1 to 4 cm square. The marker 39 is for example an optical marker distance sensor and is fixed to the olecranon part of the elbow joint 14.

The stretch sensors 40, 41, and 42 have a first end disposed on the body surface of the upper arm 12 connected to one side of the elbow joint (joint) 14 of the subject 1. The stretch sensors 40, 41, and 42 have a second end disposed on the body surface of the front arm 11 connected to the elbow joint 14 on the side opposite to the upper arm 12. The stretch sensors 40, 41, and 42 are configured similarly to the stretch sensors 34 and 36.

The fixture 3 is made of a relatively high elastic fiber material. The fixture 3 has a cylindrical shape removable from the arm 10 of the subject 1. More specifically, the fixture 3 extends to above the wrist joint 15 from the base of the upper arm 12 of the subject 1 and stretches and contracts with the motion of the elbow joint 14. With the fixture 3 attached to the subject 1, a portion corresponding to the elbow joint 14 (specifically, a portion including the central portion in the length direction of the fixture 3) is provided with the above three stretch sensors 40, 41, and 42. Note that the stretch sensors 40, 41, and 42 may be attached by using a fixture 3 of a two-layer structure and including the stretch sensors 40, 41, and 42 between the layers or by attaching the stretch sensors 40, 41, and 42 to the surface of the fixture 3. In any case, the stretch sensors 40, 41, and 42 are fixed such that they cannot be displaced relative to the fixture 3.

The three stretch sensors 40, 41, and 42 have respective first ends 40A, 41A, and 42A disposed on the body surface on a first side (the upper arm 12 side) relative to the elbow joint 14 in the length direction of the fixture 3. The three stretch sensors 40, 41, and 42 have respective second ends 40B, 41B, and 42B disposed on the body surface on a second side (the front arm 11 side) relative to the elbow joint 14 in the length direction of the fixture 3. Therefore, when the subject 1 moves the elbow joint 14, the stretch sensors 40, 41, and 42 and the fixture 3 stretch and contract with the displacement of the body surface around the elbow joint 14.

The first ends 40A, 41A, and 42A of the stretch sensors 40, 41, and 42 are spaced from the front side (chest side) toward the rear side (back side) of the body on the upper arm 12. The stretch sensors 40, 41, and 42 extend in directions in which they intersect each other. In other words, the stretch sensors 40, 41, and 42 are not parallel. The stretch sensors 40, 41, and 42 intersect in a virtual straight line that joins the upper arm 12, the elbow joint 14, and the front arm 11 when the elbow joint 14 is stretched.

In this embodiment, the stretch sensor 40 intersects with the stretch sensor 42 on the front arm 11. The stretch sensor 41 intersects with the stretch sensor 42 on the front arm 11. Although the stretch sensors 40 and 41 do not intersect, they approach each other as they go from the upper arm 12 side toward the front arm 11 side. In other words, the stretch sensors 40 and 41 extend such that their extensions intersect on the front arm 11. Therefore, the second end 42B of the stretch sensor 42 is fixed on the front side of the front arm 11 relative to the second ends 40B and 41B of the stretch sensors 40 and 41.

The relay system 35 is electrically connected to the bioelectrodes 37 and 38 and the stretch sensors 40, 41, and 42. The relay system 35 sends to the information providing system 20 an electrical signal (specifically, biological information and a capacitance change) delivered from the bioelectrodes 37 and 38 and the stretch sensors 40, 41, and 42. It is preferable to communicate between the relay system 35 and the information providing system 20 using, by way of example, a wireless communication that is compliant with the Bluetooth (registered trademark) specification.

Figure 8:
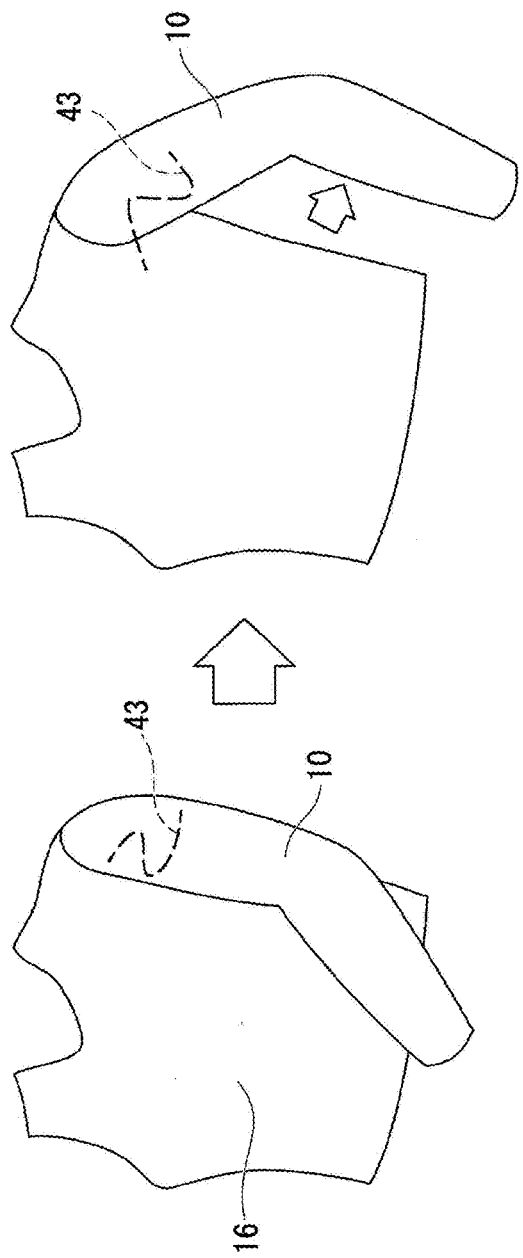
FIG. 8 illustrates an example of an arm motion detected by a stretch sensor.
Figure 9:
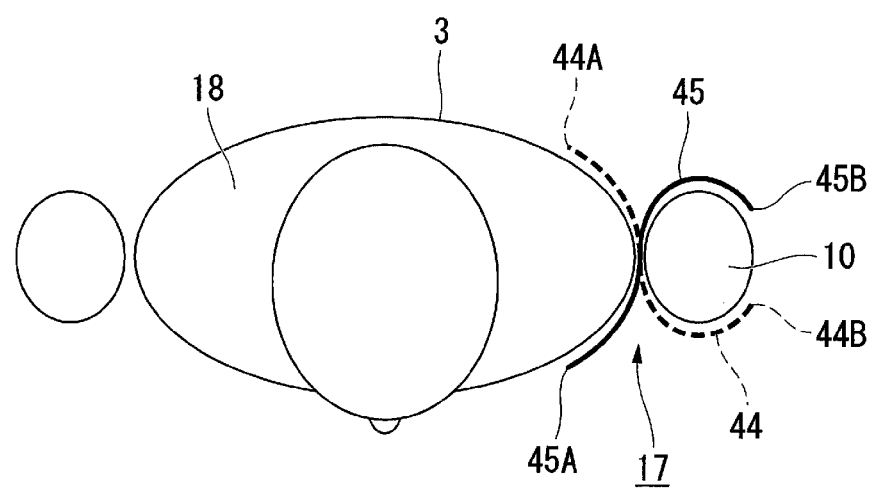
FIG. 9 illustrates a glenohumeral joint in a reference position.

FIG. 8 illustrates an example of an arm motion detected by a stretch sensor 43. The stretch sensor 43 stretches when a state in which the arm 10 is near (for example, close to) the trunk 16, as shown in the left of FIG. 8, is changed to a state in which the arm 10 is away from trunk 16, as shown in the right of FIG. 8. In the swinging motion, for identifying the armpit tightening (supination limitation) in which the stretch sensor 43 stretches by the advance and twisting of the upper arm, the both two stretches in the case where supination (raise of upper arms) occurs using two intersecting stretch sensors are used as shown in FIG. 9. The advance and twisting of the upper arm from the raise of upper arms (supination) can be distinguished from significant stretch of one of the two elastic stretch sensors in the advance and twisting.

FIG. 9 shows a state in which a glenohumeral joint 17 is in the reference position (specifically, a state in which the arm 10 stretches straight downward). After wearing the sensor 1C, the subject initializes, as necessary, the determination unit described in the first embodiment, while holding the reference position.

When supinating the arm 10 from the reference position (specifically, when raising the arm 10 laterally away from the body), the stretch sensors 44 and 45 stretch and contraction, as shown in FIG. 9. On the basis of the difference of the amount of stretch between the stretch sensors 44 and 45, the information providing system 20 senses that the glenohumeral joint 17 is displaced to abduction and detects the amount of the motion. The subject 1 may know the supination occurrence and the amount thereof and rate his/her motion.

Additionally, although not shown in detail, when pronating the arm 10 from the reference position (specifically, when raising the arm 10 overlapping the front side of the body), the stretch sensors 44 and 45 stretch and contraction. On the basis of the difference of the amount of stretch between the stretch sensors 44 and 45, the information providing system 20 senses that the glenohumeral joint 17 is displaced to adduction and detects the amount of the motion. The subject 1 may know the pronation occurrence and the amount thereof and rate his/her motion.

The information providing system 20 in the second embodiment operates similarly to the information providing system 20 in the first embodiment except that the sensors provide more types of information and the learning unit 202 learns using learning data according to the types. Therefore, its specific description is omitted here.

The exercise rating and improvement system 100 thus configured in the second embodiment may provide effects similar to those in the first embodiment.

Figure 10:
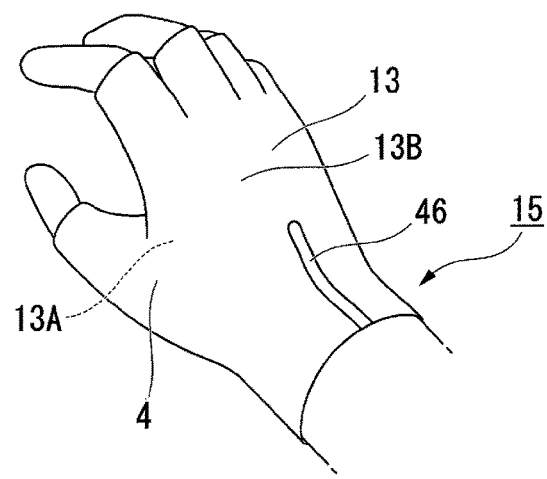
FIG. 10 illustrates an example of sensors in an exercise rating and improvement system according to a third embodiment.

(Third Embodiment) FIG. 10 illustrates an example of a sensor in an exercise rating and improvement system 100 according to a third embodiment. The exercise rating and improvement system 100 according to the third embodiment includes, in addition to the information providing system 20, a stretch sensor 46 attached to the subject 1 and the relay system 35 (not shown in FIG. 10). The exercise rating and improvement system 100 in this embodiment is used to rate and improve the motion of the wrist joint (wrist) 15. Therefore, the sensor in the third embodiment is attached to the wrist joint 15 of the subject 1.

As shown in FIG. 10, the sensor in this embodiment includes the stretch sensor 46 contained in a glove-shaped fixture 4. The stretch sensor 46 is fixed to a dorsum manus 13B by the fixture 4. In addition, in third embodiment, the relay system 35 is fixed around the upper arm 12.

FIG. 10 shows a state in which the wrist joint 15 is in the reference position (specifically, a state in which the wrist joint 15 stretches straight). Here, when the subject 1 plays golf swing, for example, the wrist joint 15 may be displaced to the dorsiflex posture. Note that the dorsiflex posture refers to a posture in which the wrist joint 15 is bent toward the dorsum manus 13B.

When the wrist joint 15 is displaced from the basic position to the dorsiflex posture, the stretch sensor 46 stretches and contracts. On the basis of the amount of stretch of the stretch sensor 46, the information providing system 20 senses that the wrist joint 15 is displaced to the dorsiflex posture and detects the amount of the motion.

Meanwhile, although not shown in detail, also when the wrist joint 15 is displaced to the palmar flexion (specifically, a posture in which the wrist joint 15 is bent toward the palm 13A) opposite to the dorsiflex posture, the stretch sensor 46 stretches and contracts similarly. On the basis of the amount of stretch of the stretch sensor 46, the information providing system 20 senses that the wrist joint 15 is displaced to palmar flexion and detects the amount of the motion. From the above, the subject 1 may know the motion of the wrist joint 15 and the amount thereof and rate his/her motion.

The motion of the information providing system. 20 in the third embodiment is similar to that of the information providing system 20 in the first embodiment. Therefore, its specific description is omitted here.

The exercise rating and improvement system 100 thus configured in the third embodiment may provide effects similar to those in the first embodiment.

Figure 11:
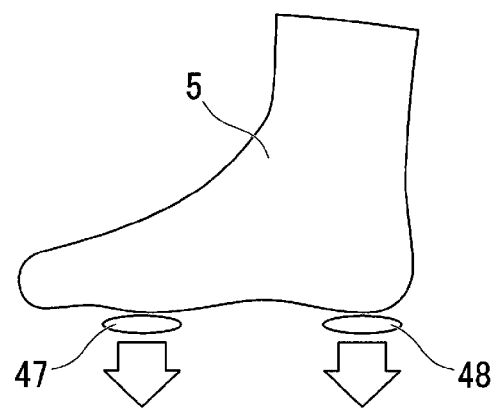
FIG. 11 illustrates an example of sensors in an exercise rating and improvement system according to a fourth embodiment.

(Fourth Embodiment) FIG. 11 illustrates an example of sensors in an exercise rating and improvement system 100 according to a fourth embodiment. The exercise rating and improvement system 100 in the fourth embodiment includes, in addition to the information providing system 20, a plurality of foot pressure sensors 47 and 48 attached to the subject 1 and the relay system 35 (not shown in FIG. 11). The exercise rating and improvement system. 100 in this embodiment is used to rate and improve the motion of a foot. Therefore, the sensor in the fourth embodiment is attached to a foot of the subject 1.

The sensor includes a plurality of (two in this embodiment) foot pressure sensors 47 and 48 and a fixture (sock) 5 that provides the foot pressure sensor 47 and 48 externally. As shown in FIG. 11, the foot pressure sensor 47 and 48 are fixed to the plantar part of the subject 1 by the fixture 5. The foot pressure sensor 47 and 48 measure the pressure (hereinafter referred to "plantar pressure") applied to the plantar part of the subject 1. The foot pressure sensor 47 and 48 have a rectangular flat configuration and are provided at or near a site of the plantar part which is applied with a pressure of a threshold or more. For example, the foot pressure sensor 47 and 48 are provided at or near a site of the plantar part which is applied with the highest pressure. The site applied with the highest pressure includes, for example, the thumb ball, hypothenar, calcaneus, and toe. The foot pressure sensors 47 and 48 send the measurement results to the relay system 35. In addition, in the fourth embodiment, the relay system 35 is fixed near the thigh.

The information providing system 20 in the fourth embodiment operates similarly to the information providing system 20 in the first embodiment except that the sensors provide different types of information and the learning unit 202 learns using learning data according to the types. Therefore, its specific description is omitted here.

The exercise rating and improvement system 100 thus configured in the fourth embodiment may provide effects similar to those in the first embodiment.

Figure 12:
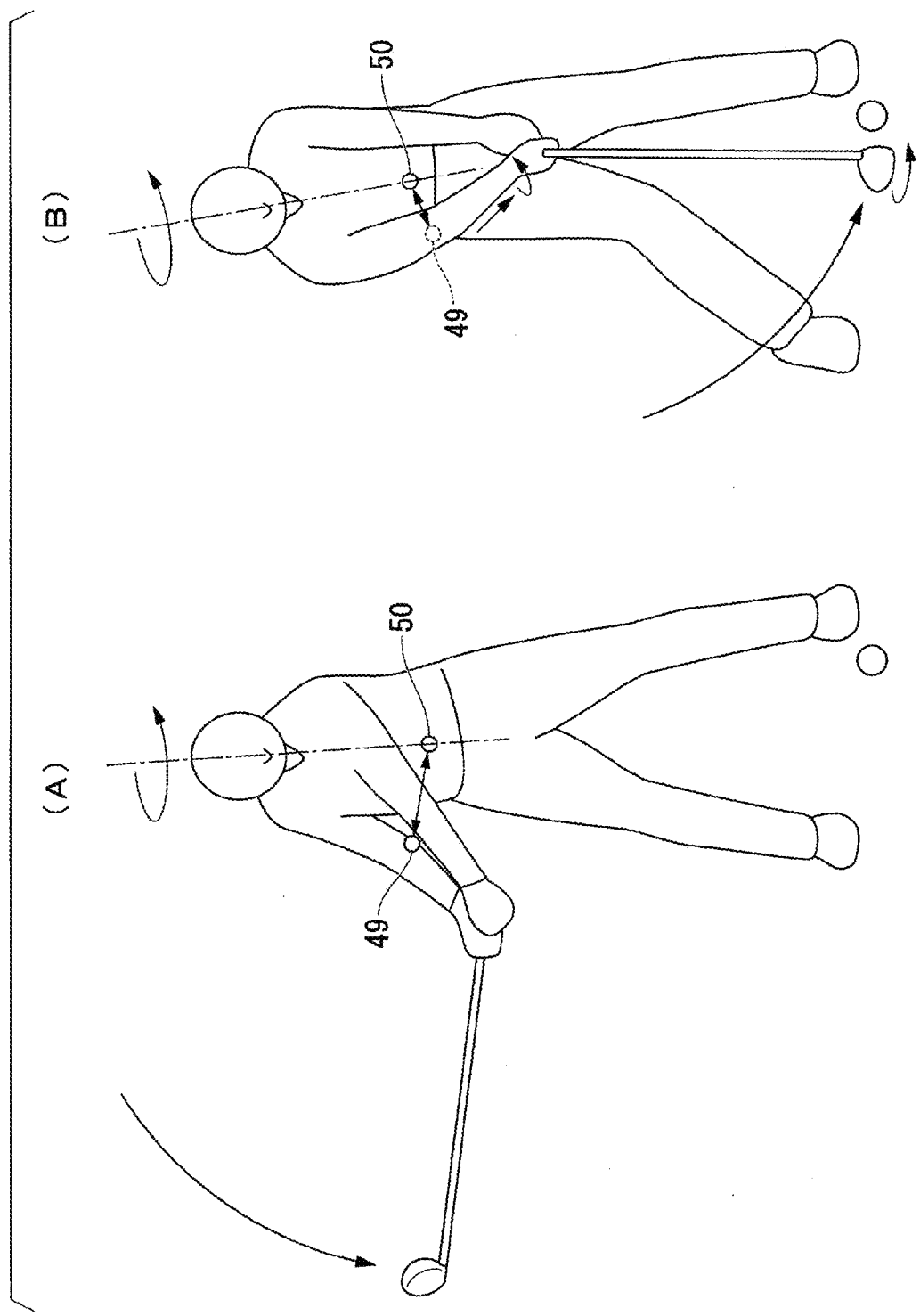
FIG. 12 illustrates an example of sensors in an exercise rating and improvement system according to a fifth embodiment.

(Fifth Embodiment) FIG. 12 illustrates an example of sensors in an exercise rating and improvement system 100 according to a fifth embodiment. The exercise rating and improvement system 100 in the fifth embodiment includes, in addition to the information providing system 20, first and second devices 49 and 50 attached to the subject 1 and the relay system 35 (not shown in FIG. 12). The exercise rating and improvement system 100 in this embodiment is used to rate and improve the distance between a plurality of sites of the subject in motion.

The first and second devices 49 and 50 are attached to respective sites of two points between which distance is to be measured. For example, the first device 49 is attached to the reference site and the second device 50 is attached to a site the distance of which is to be measured from the reference site. FIG. 12 shows an example to rate and improve the distance between the elbow joint and the trunk on the downswing. Therefore, the sensors in the fifth embodiment are attached to the elbow and trunk of the subject 1. FIG. 12 shows an example where the first device 49 is attached to the right elbow and the second device 50 is attached to the trunk (abdominal part). FIG. 12 (A) shows a motion on the downswing. FIG. 12 (B) shows a motion on the piston snap (extension and pronation of the right elbow joint).

The sensor includes the first and second devices 49 and 50. The first device 49 outputs a sound wave or radio wave. For example, the first device 49 is a speaker or transmitter. The second device 50 receives the sound wave or radio wave output from the first device 49. For example, the second device 50 is a microphone or receiver. The second device 50 outputs the received sound wave or radio wave to the relay system 35.

The relay system 35 is electrically connected to the first and second devices 49 and 50. The relay system 35 sends to the information providing system 20 an electrical signal (specifically, a sound wave or radio wave) delivered from the second device 50. It is preferable to communicate between the relay system 35 and the information providing system 20 using, by way of example, a wireless communication that is compliant with the Bluetooth (registered trademark) specification.

The information providing system 20 in the fifth embodiment calculates the distance between the two points on the basis of the obtained information. The information providing system 20 then determines whether the right elbow is away from the trunk on the downswing by comparing the calculation result and the model, and provides the rating result and improvement information.

The timing when the motion starts may be informed by sound through a speaker of the relay system 35 or the sensor or by light from LED or the like of the relay system 35 or the sensor.

Figure 13:
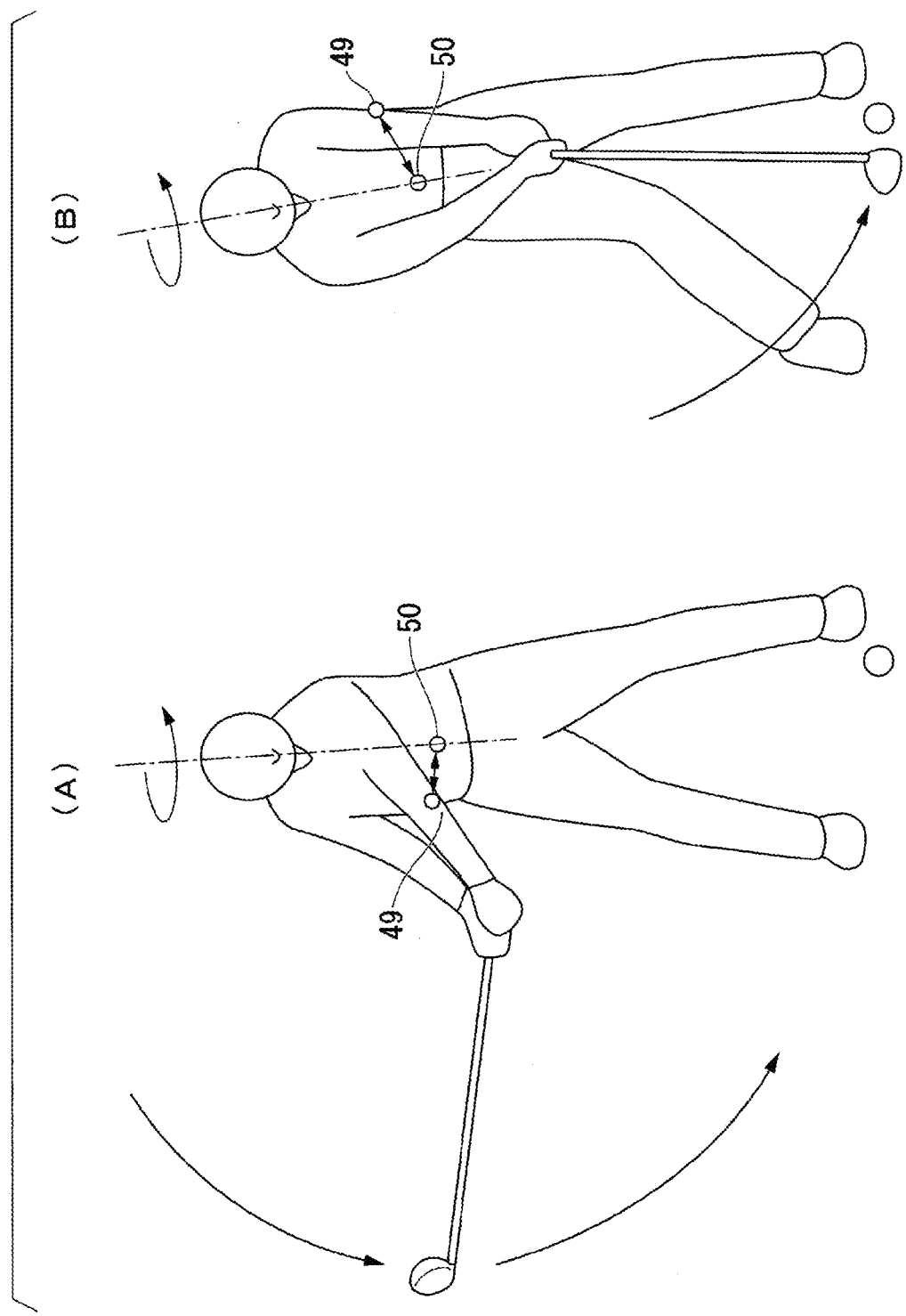
FIG. 13 illustrates another example of sensors in the exercise rating and improvement system 100 according to the fifth embodiment.

FIG. 13 illustrates another example of sensors in the exercise rating and improvement system 100 according to the fifth embodiment. FIG. 13 shows an example where the first device 49 is attached to the left elbow and the second device 50 is attached to the trunk (abdominal part).

The information providing system 20 in the fifth embodiment calculates the distance between the two points on the basis of the obtained information. The information providing system 20 then determines whether the left elbow is away from the trunk on the downswing to the impact by comparing the calculation result and the model, and provides the rating result and improvement information.

The exercise rating and improvement system 100 thus configured in the fifth embodiment may provide effects similar to those in the first embodiment.

<Modification Example> The information providing system 20 may rate the subject 1 by acquiring the positions and trajectories of the elbow using a marker fixed on the elbow.

<Modification Example Common to First to Fifth Embodiments> Although the above embodiments show a configuration of generating a model by learning with supervised data, the information providing system 20 may also be configured to generate a model by learning with unsupervised data. Any or all of the first to fifth embodiments may be configured to be combined.

While the embodiments of this invention have been described in detail with respect to the drawings, specific configurations are not limited to these embodiments and any design may also be included without departing from the spirit of the invention.

REFERENCE SIGNS LIST

20 Information providing system
32, 33, 37, 38 Bioelectrode
35 relay system
34, 36, 40, 41, 42, 43, 44, 45, 46 Stretch sensor
47, 48 Foot pressure sensor
49 First device
50 Second device
201 Input unit
202 Learning unit
203 Model storage unit
204 Acquisition unit
205 Feature amount extraction unit
206 Rating unit
207 Improvement information providing unit
208 Rating result storage unit
209 Improvement situation providing unit

The invention claimed is:

1. A computer-implemented method for rating an operation using electrical signals, the method comprising:
receiving the electrical signals from one or more sensors attached to a subject exercising a sport, wherein the electrical signals are associated with the subject in operation associated with exercising the sport, the electrical signals relating to one or more of biological data and movement data of the subject represented by the electrical signals from the one or more sensors attached to the subject while exercising the sport;
extracting from the electrical signals associated with the subject exercising the sport, based on a trained machine learning model, a feature amount of exercise efficiency of the subject exercising the sport, wherein the trained machine learning model is trained using supervised training data associated with an advanced player exercising the sport, wherein the supervised training data includes the feature amount of the exercise efficiency of the subject indicating rating indices corresponding to at least one of motion, position, timing between motions, strength, or tension associated with exercising the sport, and wherein the advanced player is distinct from the subject;
determining a rating associated with the exercise efficiency of the subject based at least on a comparison between the feature amount of the exercise efficiency of the subject and a target feature amount of exercise efficiency associated with the advanced player exercising the sport;
generating information associated with the rating including the exercise efficiency of the subject, wherein the information is associated with eliminating a difference between the feature amount of the exercise efficiency of the subject and the target feature amount of exercise efficiency; and
outputting at least one of sound or light based on the rating associated with the exercise efficiency of the subject and the information.

2. The computer-implemented method of claim 1, the method further comprising:
extracting, the feature amount of the exercise efficiency of the subject using the trained learning model trained on exercising the sport, the sport including golf.

3. The computer-implemented method of claim 1, wherein the rating associated with the exercise efficiency of the subject is positive when a difference between the feature amount of the exercise efficiency of the subject and the target feature amount of exercise efficiency associated with the advanced player is within a predetermined threshold, and wherein the information indicates one or more ways to eliminating the difference.

4. The computer-implemented method of claim 1, the method further comprising:
  receiving data associated with the advanced player in the operation, wherein the data associated with the advanced player include one or more of:
    the one or more of biological data of the advanced player using a first sensor,
    the movement data of one or more joints of the advanced player using a second sensor,
    data on a pressure applied on a plantar part of the advanced player using a third sensor, and
    data indicating a distance between a first point as a reference point and a second point on a body surface of the advanced player using a fourth sensor;
  generating the supervised training data based on the data associated with the advanced player;
  training a machine learning model using the supervised training data; and
  generating the target feature amount of exercise efficiency associated with the advanced player in the operation using the machine learning model.

5. The computer-implemented method of claim 1, wherein the electrical signals of the subject include one or more of:
  the one or more of biological data of the subject using a first sensor,
  the movement data of one or more joints of the subject using a second sensor,
  data on a pressure applied on a plantar part of the subject using a third sensor, and
  data indicating a distance between a first point on a body surface of the subject as a reference point and a second point on the body surface of the subject using a fourth sensor, and
  wherein one or more of the first sensor, the second sensor, the third sensor, and the fourth sensor, are one or more parts of one or more fixtures covering at least a part of the body surface of the subject.

6. The computer-implemented method of claim 5, wherein the one or more fixtures include a removable arm cover extending from a base of an upper arm to above a wrist joint of the subject, stretching and contracting with an elbow joint movement without displacing the one or more of the one or more sensors including the first sensor, the second sensor, the third sensor, or the fourth sensor, against the body surface of the subject.

7. The computer-implemented method of claim 6, wherein the operation relates to performing a golf swing operation, wherein the rating associated with the exercise efficiency relates to bending and stretching of an elbow joint of the subject, and wherein the information relates to bending of the elbow joint as a downswing motion of the golf swing operation starts.

8. A system for rating an operation using electrical signals, the system comprising:
  a processor; and
  a memory storing computer-executable instructions that when executed by the processor cause the system to:
    receive the electrical signals from one or more sensors attached to a subject exercising a sport, wherein the electrical signals are associated with the subject in operation associated with exercising the sport, the electrical signals relating to one or more of biological data and movement data of the subject represented by the electrical signals from the one or more sensors attached to the subject while exercising the sport;
    extract from the electrical signals associated with the subject exercising the sport, based on a trained machine learning model, a feature amount of exercise efficiency of the subject exercising the sport, wherein the trained machine learning model is trained using supervised training data associated with an advanced player exercising the sport, wherein the supervised training data includes the feature amount of the exercise efficiency of the subject indicating rating indices corresponding to at least one of motion, position, timing between motions, strength, or tension associated with exercising the sport, and wherein the advanced player is distinct from the subject;
    determine a rating associated with the exercise efficiency of the subject based at least on a comparison between the feature amount of the exercise efficiency of the subject and a target feature amount of exercise efficiency associated with the advanced player exercising the sport;
    generate information associated with the rating including the exercise efficiency of the subject, wherein the information is associated with eliminating a difference between the feature amount of the exercise efficiency of the subject and the target feature amount of exercise efficiency associated with the advanced player exercising the sport; and
    output at least one of sound or light based on the rating associated with the exercise efficiency of the subject and the information.

9. The system of claim 8, the computer-executable instructions when executed further causing the system to:
  extract the feature amount of the exercise efficiency of the subject, wherein the feature amount indicates a combination of an elbow joint bending at a time and the elbow joint bending at another time.

10. The system of claim 8, wherein the rating associated with the exercise efficiency is positive when a difference between the feature amount of exercise efficiency of the subject and the target feature amount of exercise efficiency associated with the advanced player is within a predetermined threshold, and wherein the information indicates one or more ways to eliminating the difference.

11. The system of claim 8, the computer-executable instructions when executed further causing the system to:
  receive data associated with the advanced player in the operation, wherein the data associated with the advanced player include one or more of:
    the one or more of biological data of the advanced player using a first sensor,
    the movement data of one or more joints of the advanced player using a second sensor,
    data on a pressure applied on a plantar part of the advanced player using a third sensor, and
    data indicating a distance between a first point as a reference point and a second point on a body surface of the advanced player using a fourth sensor;

generate the supervised training data based on the data associated with the advanced player;

train a machine learning model using the supervised training data; and generate the target feature amount of exercise efficiency associated with the advanced player in the operation using the trained machine learning model.

12. The system of claim 8, wherein the information of the subject includes one or more of:

the one or more of biological data of the subject using a first sensor, the movement data of one or more joints of the subject using a second sensor, data on a pressure applied on a plantar part of the subject using a third sensor, and data indicating a distance between a first point on a body surface of the subject as a reference point and a second point on the body surface of the subject using a fourth sensor, and wherein one or more of the first sensor, the second sensor, the third sensor, and the fourth sensor, are one or more parts of one or more fixtures covering at least a part of the body surface of the subject.

13. The system of claim 8, wherein the one or more fixtures include a removable arm cover extending from a base of an upper arm to above a wrist joint of the subject, stretching and contracting with an elbow joint movement without displacing sensors against a body surface of the subject.

14. The system of claim 13, wherein the operation relates to performing a golf swing operation, wherein the rating associated with the exercise efficiency relates to bending and stretching of an elbow joint of the subject, and wherein the information indicates bending of the elbow joint as a downswing motion of the golf swing operation starts.

15. A computer-readable non-transitory recording medium storing computer-executable instructions that when executed by a processor cause a computer system to:

receive electrical signals from one or more sensors attached to a subject exercising a sport, wherein the electrical signals are associated with the subject in operation associated with exercising the sport, the electrical signals relating to one or more of biological data and movement data of the subject represented by the electrical signals from the one or more sensors attached to the subject while exercising the sport;

extract from the electrical signals associated with the subject exercising the sport based on a trained machine learning model, a feature amount of exercise efficiency of the subject exercising the sport, wherein the trained machine learning model is trained using supervised training data associated with an advanced player exercising the sport, wherein the supervised training data includes the feature amount of the exercise efficiency of the subject indicating rating indices associated with exercising the sport, and wherein the advanced player is distinct from the subject determine a rating associated with the exercise efficiency of the subject based at least on a comparison between the feature amount of the exercise efficiency of the subject and a target feature amount of exercise efficiency associated with the advanced player exercising the sport;

generate information associated with the rating including the exercise efficiency of the subject, wherein the information is associated with eliminating a difference between the feature amount of the exercise efficiency of the subject and the target feature amount of exercise efficiency; and output at least one of sound or light based on the rating associated with the exercise efficiency of the subject and the information.

16. The computer-readable non-transitory recording medium of claim 15, wherein the rating associated with the exercise efficiency is positive when a difference between the feature amount of the exercise efficiency of the subject and the target feature amount of the exercise efficiency associated with the advanced player is within a predetermined threshold, and wherein the information indicates one or more ways to eliminating the difference.

17. The computer-readable non-transitory recording medium of claim 15, the computer-executable instructions when executed further causing the system to:

receive data associated with the advanced player in the operation, wherein the data associated with the advanced player includes one or more of:

the one or more of biological data of the advanced player using a first sensor, the movement data of one or more joints of the advanced player using a second sensor, data on a pressure applied on a plantar part of the advanced player using a third sensor, and data indicating a distance between a first point as a reference point and a second point on a body surface of the advanced player using a fourth sensor;

generate the supervised training data based on the data associated with the advanced player;

train a machine learning model using the supervised training data; and generate the target feature amount of exercise efficiency associated with the advanced player in the operation using the trained machine learning model.

18. The computer-readable non-transitory recording medium of claim 15, wherein the information of the subject includes one or more of:

the one or more of biological data of the subject using a first sensor, the movement data of one or more joints of the subject using a second sensor, data on a pressure applied on a plantar part of the subject using a third sensor, and data indicating a distance between a first point on a body surface of the subject as a reference point and a second point on the body surface of the subject using a fourth sensor, and wherein one or more of the first sensor, the second sensor, the third sensor, and the fourth sensor, are one or more parts of one or more fixtures covering at least a part of the body surface of the subject.

19. The computer-readable non-transitory recording medium of claim 15, wherein the one or more fixtures include a removable arm cover extending from a base of an upper arm to above a wrist joint of the subject, stretching and contracting with an elbow joint movement without displacing sensors against a body surface of the subject.

20. The computer-readable non-transitory recording medium of claim 19, wherein the operation relates to performing a golf swing operation, wherein the rating associated with the exercise efficiency relates to bending and stretching of an elbow joint of the subject, and wherein the information includes a direction to bending of the elbow joint as a downswing motion of the golf swing operation starts.

* * * * *